(12) United States Patent
Casey et al.

(10) Patent No.: US 8,158,164 B2
(45) Date of Patent: Apr. 17, 2012

(54) EDIBLE COMPOSITION FOR TREATING CUTANEOUS SIGNS OF AGEING

(75) Inventors: John Casey, Sharnbrook (GB); Gail Jenkins, Sharnbrook (GB); Linda Jane Wainwright, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 197 days.

(21) Appl. No.: 12/707,706

(22) Filed: Feb. 18, 2010

(65) Prior Publication Data

US 2010/0215762 A1 Aug. 26, 2010

(30) Foreign Application Priority Data

Feb. 23, 2009 (EP) ..................................... 09153407

(51) Int. Cl.
*A01N 65/00* (2009.01)
(52) U.S. Cl. ........................................................ 424/725
(58) Field of Classification Search ........................ None
See application file for complete search history.

(56) References Cited

U.S. PATENT DOCUMENTS

| | | | |
|---|---|---|---|
| 6,086,910 A | 7/2000 | Howard et al. | |
| 6,200,601 B1 | 3/2001 | Gorenbein et al. | |
| 7,282,225 B1 | 10/2007 | Davis et al. | |
| 2001/0002407 A1 | 5/2001 | Nair et al. | |
| 2002/0037855 A1 | 3/2002 | Stanislaus | |
| 2003/0108593 A1 | 6/2003 | Oku et al. | |
| 2003/0108624 A1 | 6/2003 | Kosbab | |
| 2004/0096479 A1 | 5/2004 | Levine | |
| 2004/0109905 A1 | 6/2004 | Bagchi | |
| 2004/0116514 A1 | 6/2004 | Nishino et al. | |
| 2004/0146539 A1 | 7/2004 | Gupta | |
| 2004/0180102 A1 | 9/2004 | Patt | |
| 2005/0037038 A1 | 2/2005 | Gupta | |
| 2005/0048008 A1 | 3/2005 | Gupta | |
| 2005/0147648 A1 | 7/2005 | Gierhart | |
| 2006/0045896 A1 | 3/2006 | Morariu | |
| 2006/0089411 A1 | 4/2006 | Gierhart | |
| 2006/0234948 A1 | 10/2006 | Empie et al. | |
| 2006/0280762 A1 | 12/2006 | Kostick et al. | |
| 2007/0196349 A1 | 8/2007 | Kitamura et al. | |
| 2007/0286930 A1 | 12/2007 | Ogawa et al. | |
| 2008/0199564 A1 | 8/2008 | Boghani et al. | |
| 2008/0207774 A1 | 8/2008 | Krishnan | |

FOREIGN PATENT DOCUMENTS

| | | |
|---|---|---|
| CN | 1957886 | 5/2007 |
| CN | 1957903 | 5/2007 |
| JP | 62-048611 | 3/1987 |
| JP | 2001-240527 | 4/2001 |
| JP | 2004-107245 | 4/2004 |
| JP | 2007-308396 | 11/2007 |
| JP | 2008-110933 | 5/2008 |
| WO | 03/039452 | 5/2003 |
| WO | 2007/140022 | 12/2007 |
| WO | 2008/073664 | 6/2008 |

OTHER PUBLICATIONS

European Search Report on Application No. EP 09 15 3407 dated Sep. 3, 2009.
Lisa Drayer: "The Beauty Diet: Looking Great Has Never Been So Delicious", 2008, XP002543061, pp. 23-25.

*Primary Examiner* — Michael Meller
(74) *Attorney, Agent, or Firm* — Milton L. Honig

(57) ABSTRACT

This invention relates to the provision of an edible composition for the treatment of cutaneous signs of ageing, in particular those associated with loss of skin elasticity, wrinkles and sagging. Thus the inventive composition provides skin benefits selected from the group consisting of enhancing collagen deposition in the skin, reducing the appearance of wrinkles and reducing sagging. Thus the invention provides an edible composition for treating aged skin, the composition comprising:

(a) 2 to 1000, preferably 5 to 750, most preferably 10 to 500 mg anthocyanidin and derivatives thereof; and
(b) 1 to 20, preferably 5 to 15, most preferably 2 to 10 mg lutein and derivatives thereof;

wherein the weight ratio of anthocyanidin to lutein is at least 1:1, preferably at least 10:1 and more preferably at least 25:1, even more preferably at least 50:1, most preferably at least 100:1;

wherein the composition excludes copper in the form of separately or in combination copper gluconate and copper oxide;

and further excludes separately or in combination with the copper exclusion Nandina domestica or an extract thereof.

The invention also relates to a cosmetic method for providing the aforesaid skin benefits using the inventive composition.

2 Claims, 1 Drawing Sheet

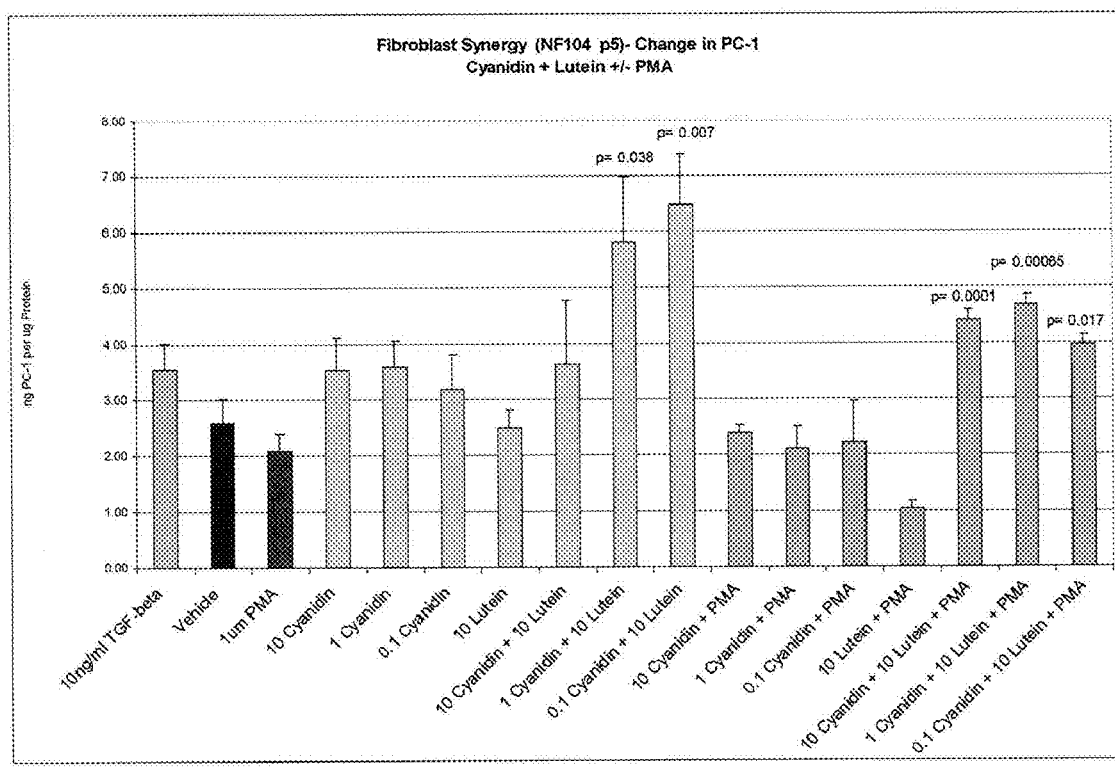

EDIBLE COMPOSITION FOR TREATING CUTANEOUS SIGNS OF AGEING

This invention relates to the provision of an edible composition for the treatment of cutaneous signs of ageing, in particular those associated with loss of skin elasticity, wrinkles and sagging. Thus the inventive composition provides skin benefits selected from the group consisting of enhancing collagen deposition in the skin, reducing the appearance of wrinkles and reducing sagging. The invention also relates to a cosmetic method for providing the aforesaid skin benefits.

SUMMARY OF THE INVENTION

In a first aspect of the invention, an edible composition for treating aged skin is provided, the composition comprising:
(a) 2 to 1000, preferably 5 to 750, most preferably 10 to 500 mg anthocyanidin and derivatives thereof; and
(b) 1 to 20, preferably 2 to 15, more preferably 2 to 10, most preferably 3 to 10 mg lutein and derivatives thereof;
wherein the weight ratio of anthocyanidin to lutein is at least 1:1, preferably at least 10:1 and more preferably at least 25:1, even more preferably at least 50:1, most preferably at least 100:1;
wherein the composition excludes copper in the form of separately or in combination copper gluconate and copper oxide; and further excludes separately or in combination with the copper exclusion Nandina domestica or an extract thereof.

The basis for this invention originates from the observation by the inventors that anthocyanidin and lutein operate synergistically to provide increased levels of type 1 procollagen, a precursor of type 1 collagen. As the amount of type 1 procollagen reflects stoichiometrically the amount of type 1 collagen synthesised, the synthesis of type 1 procollagen can therefore be considered as a marker for type 1 collagen synthesis. Type 1 collagen is the most abundant of the numerous collagen types and is found, in particular, in the skin. Bundles of collagen, known as collagen fibres, are a major component of the extracellular matrix that supports most tissues and gives cells structure from the outside. Type 1 collagen, in particular, is a major component of skin and is responsible for giving skin its strength and elasticity. Thus its degradation, with age, leads to wrinkles and sagging. Thus use of the inventive composition will lead to improvement in skin elasticity and reduction in the appearance of wrinkles and sagging.

The term "derivatives thereof" when referring to anthocyanidin is intended to include the related anthocyanin derivatives, examples of which are glucoside, rutinoside and sophoroside.

By the term "edible" is meant edible by a human. The composition may be in the form of an emulsion in combination or not with milk solids.

The anthocyanidin may be selected from the group consisting of aurantindin, cyanidin, delphinidin, europindin, luteolindin, pelargonidin, malvidin, peonidin, petunidin and rosindin. Preferably the anthocyanidin is cyanidin. Optionally the derivative of the anthocyanidin is an anthocyanin.

Typically cyanidin itself will be present either alone or in combination with one or more other anthocyanidin type compounds. Often when cyanidin is present, the compounds cyanin, idaein, keracyanin, asterin and their derivatives are present in trace amounts only as would be common for natural plant extracts of a substance. For instance, the related compounds may be present in less than 1%, preferably less than 0.2%, often less than 0.05%, more often less than 0.01% by weight of the cyanidin component of the inventive composition. It is preferred that where cyanidin is present in combination with other anthocyanidin compounds, that the cyanidin will be present as more than 50%, preferably more than 75% by weight of the anthocyanidin component.

Anthocyanidins including cyanidin are pigments found in many red berries including but not limited to bilberry, blackberry, blueberry, cherry, cranberry, elderberry, hawthorn, loganberry, acai berry and raspberry. They can also be found in other fruits such as apples and plums. The highest concentrations of anthocyanidins are found in the skin of the fruit.

The derivative of lutein may be an ester thereof.

The composition preferably comprises one or more additional components selected from the group consisting of antioxidants, flavouring agents, preservatives and stabilisers.

The inventive composition may take any suitable form, including, for example food products and nutritional supplements. Compositions for oral consumption include beverages, bars and other liquid and solid forms such as tablets, pills, capsules and powders (which may contain crystalline material), as well as spreads, margarines, creams, sauces, dressings, mayonnaises, ice creams, fillings, confectionaries and cereals. The inventive composition may also be sold in the form of a kit with a topical composition, the topical composition having the same skin care benefits selected from the group consisting of enhancing collagen deposition in the skin, reducing the appearance of wrinkles and reducing sagging. Thus such a kit comprising an edible composition for treating aged skin according to the inventive composition and a topical composition as mentioned hereinabove can, when in use, then act both from "inside" and "outside" the skin to provide the skin care benefits selected from the group consisting of enhancing collagen deposition in the skin, reducing the appearance of wrinkles and reducing sagging.

In one embodiment, the inventive composition is preferably water based, i.e. comprises at least 50% water, preferably at least 60% or even at least 70% w/w water. It may be either liquid or frozen. The product thus has the sensation of being a regular water-based product and can be consumed on a regular basis as part of a consumer's normal diet. For example it could replace a fruit juice normally consumed at breakfast time. The inventive composition is preferably packaged as a beverage, for example, in a container such as a carton or a bottle of coated paper or cardboard, glass or plastic. The container preferably has a volume of from 10 to 500 ml, such as from 20 to 100 ml.

In an alternative embodiment, the inventive composition is contained in a capsule, provided together with instructions informing the user of a proposed dosage regime.

The capsule may be made of any suitable material well known in the art such as gelatin. The capsule is adapted to be swallowed by the consumer and typically one or two capsules will be taken from one to four times per day.

Alternatively the inventive composition may be included as one component of a complex food product, for instance the composition may be present in solid or gelatinous form as a filling or layer within a bar or similar product. The composition may therefore be included in a wide range of everyday food stuffs, for instance in "health food" bars which could be eaten as an alternative to other snack foods.

One or more additional antioxidants, to the anthothocyanidin and derivatives thereof which are themselves antioxidants, are preferably present in the inventive compositions in order to prevent or slow down the natural oxidative degradation of the composition. Suitable additional antioxidants can be selected, although not exclusively, from the following list, either singularly or in combination: TBHQ, ascorbyl esters (e.g. ascorbyl palmitate), ascorbic acid, tocopherols, rosemary extract, fruit concentrates or extracts, black or green tea extract, propyl gallate, butylated hydroxyanisole (BHA), butylated hydroxytoluene (BHT), citric acid or esters, tocotrienols, polyphenols, phenolic compounds, other flavonoids and oxygen scavengers. Especially preferred additional antioxidants are vitamins C and E. Not only are these effective antioxidants but they also have been shown to give skin benefits when consumed. The amount of additional antioxidant may be added in a sufficient amount to prevent the composition from going rancid over a typical shelf-life of at least 6 months. Clearly the amount of antioxidant will depend on the type and activity of the antioxidant used.

The inventive composition may comprise a flavouring, although the addition of a flavouring may be unnecessary if the lutein or anthocyanidin is provided by a flavoured substance such as a vegetable or fruit juice. Suitable flavouring agents may be natural or synthetic. Flavouring agents may be required to make the product more palatable for consumption.

The compositions may comprise an emulsifier, more preferably a food grade phospholipid emulsifier. It is preferred that the phospholipid emulsifier is lecithin. Phospholipid emulsifiers are oil soluble, but the lecithin can be added to either phase prior to emulsification. Preferably it is added to the aqueous phase. Any emulsifier is preferably present in the composition in an amount of at least 0.01%, preferably from 0.05 to 3%, more preferably from 0.1 to 1% w/w.

The composition of the invention may comprise polyunsaturated fatty acids, such as an omega-3 fatty acid (i.e. an unsaturated carboxylic acid having from 12 to 26 carbon atoms). Preferred omega-3 fatty acids are those selected from docosahexaenoic acid (DHA), eicosapentaenoic acid (EPA) and mixtures thereof. Suitable polyunsaturated fatty acids may also be selected from oleic acid, linoleic acid, γ-linoleic acid, linolenic acid, arachidonic acid. The polyunsaturated fatty acid may be present as a component of a natural oil, such as a fish oil.

The composition may also comprise soy isoflavones (including genistein or daidzein in glycosylated and/or non-glycosylated form), typically in an amount of from 0.0001 to 0.1% w/w.

The inventive composition may be made by preparing an aqueous phase and an oil phase. If an emulsifier is used, it is preferred that it is added to the aqueous phase. The oil phase and aqueous phase are then blended together to form an emulsion. In a preferred process, the oil is on a powdered carrier material to assist emulsion formation. The emulsion may then be packaged in a sealed container such as a metal, coated cardboard (e.g. Tetra Pak) or plastics container. The container is then preferably sealed so as to give no headspace or a gas-filled (e.g. nitrogen or carbon dioxide) headspace which excludes oxygen. This assists still further in preventing oxidation. Alternatively the emulsion may be frozen and packaged and sold as a frozen consumer product.

In a second aspect of the invention, a cosmetic method for providing the skin benefits selected from the group consisting of enhancing collagen deposition in the skin, improving skin elasticity, reducing the appearance of wrinkles and reducing sagging is provided, the method comprising administering the inventive composition on a daily basis in the form of at least one, preferably at least two, more preferably at least three, most preferably at least four equal or unequal servings.

In a third aspect of the invention, use of an edible composition according to the inventive composition is provided for providing the skin benefits selected from the group consisting of enhancing collagen deposition in the skin, improving skin elasticity, reducing the appearance of wrinkles and reducing sagging.

In a fourth aspect of the invention, use of an edible composition according to the inventive composition for providing the skin benefits selected from the group consisting of enhancing collagen deposition in the skin, improving skin elasticity, reducing the appearance of wrinkles and reducing sagging is provided, the use comprising administering the inventive composition on a daily basis in the form of at least one, preferably at least two, more preferably at least three, most preferably at least four equal or unequal servings.

BRIEF DESCRIPTION OF THE FIGURE

The invention is now illustrated hereinbelow with reference to:

FIG. 1 which shows concentration of type 1 procollagen in ng per μg protein for test solutions comprising lutein, cyanidin or both at various concentration given in μM.

DETAILED DESCRIPTION OF THE INVENTION

Example 1

Effect of Lutein and Cyanidin on Type 1 Procollagen Levels in Primary Human Dermal Fibroblast Cells A first set of primary human dermal fibroblast cells were cultured and passaged in Dulbecco's modified Eagle medium (DMEM), available from Gibco, supplemented with 10% foetal bovine serum (FBS). The cells were then routinely plated out in 6-well tissue culture dishes at a seeding density of ~5000 cells/cm$^2$ in 2 ml complete medium (a mixture of DMEM and FBS) per well for 24 hours and incubated at 37° C. in 5% $CO_2$. Then the complete medium was removed and the cells grown in DMEM and 1% FBS 24 hours prior to treatment. The cells were then counted, pelleted and the cell lysate assayed for type 1 procollagen-1 (PC-1) expression.

A second set of cells were prepared for assay for type 1 procollagen-1 (PC-1) expression but differing from the first set mentioned hereinabove by the fact that they were oxidatively stressed for 24 hours with a 1 mM solution of 4-beta-phorbol-12-myristate-13-acetate (PMA) (Sigma P8139) such that the final concentration of PMA was 1 μM. Then the level of cytotoxicity was determined by assaying the cell supernatant for lactate dehydrogenase (which is released on cell death). PMA mimics the effects of ultra-violet irradiation on skin cells and reduces collagen synthesis. The cells were then counted, pelleted and the cell lysate assayed for type 1 procollagen-1 (PC-1) expression.

Test solutions were prepared in DMEM containing 1% FBS and the various concentrations, given in μM, of lutein, cyanidin or both shown in FIG. 1.

The type 1 procollagen C-peptide Enzyme Immunoassay (EIA) kit, available from Takara Bio Incorporated, allows for the quantitative determination of type I procollagen C-peptide (PIP). Eight P1P standards were prepared in sample diluent at concentrations ranging from 0 to 640 ng/ml. 100 μl of antibody-peroxidase conjugate solution and either 20 μl of cell lysate (1 μg protein) or a standard were added to duplicate wells. The plate was sealed and incubated at 37° C. for 3 hours before being washed four times with 400 μl of phosphate buffer solution (PBS). Each well then received 100 μl of the substrate solution provided in the kit and the plate incubated at room temperature for 15 minutes. After this period, 100 μl of a stop solution, also provided with the kit, was added to each well and the absorbance measured at 450 nm with a plate reader. A standard curve was plotted of mean absorbance versus P1P concentration and the line of best fit calculated by regression analysis. The unknown concentrations of P1P in all the test solutions were estimated from this. The results are illustrated in FIG. 1 which clearly shows a synergistic effect on uplift in type 1 procollagen levels from the combination of lutein and cyanidin. Transforming Growth Factor Beta (TGF Beta) was used as a positive control. The vehicle was dimethyl sulphoxide (DMSO).

Example 2

Capsule Comprising Elderberry-Derived Anthocyanins and Lutein

The encapsulating process is well known to the person skilled in the art and typically comprises combining 125 mg of standardised 25% anthocyanins elderberry extract (Artemis International Inc.), 12.5 mg of a 20% dispersion of lutein in safflower oil (FloraGlo lutein 20% liquid in safflower oil available from Kemin Health LC), 8 mg of magnesium stearate and 12 mg of silica and encapsulating the mixture in a hydroxypropylmethyl cellulose (HPMC) capsule.

Two capsules were taken in the morning and a further two were taken in the evening. Visible signs of improvement to skin elasticity, reduction in the appearance of wrinkles and reduction in sagging were observed typically after 12 weeks.

Example 3

100 mg lecithin, 100 µL of a 20% dispersion of lutein in safflower oil (FloraGlo lutein 20% liquid in safflower oil available from Kemin Health LC), 4 g of standardised 25% anthocyanins elderberry extract (Artemis International Inc.) and water to make up to 100 mL were combined thereby to produce a beverage.

The beverage was prepared by first blending, in conventional emulsifier equipment, the lecithin to the water followed by the lutein and elderberry extract.

The invention claimed is:

1. An encapsulated edible emulsion for treating aged skin consisting essentially of:
   (a) 2 to 1000 mg elderberry extracted anthocyanins; and
   (b) 1 to 20 mg lutein;
   wherein the weight ratio of elderberry extracted anthocyanins to lutein is at least 1:1.

2. An encapsulated edible emulsion for treating aged skin consisting essentially of:
   (a) 2 to 1000 mg elderberry extracted anthocyanins;
   (b) 1 to 20 mg lutein; and
   (c) milk solids;
   wherein the weight ratio of elderberry extracted anthocyanins to lutein is at least 1:1.

* * * * *